US 6,696,685 B2

(12) United States Patent
Schumacher

(10) Patent No.: US 6,696,685 B2
(45) Date of Patent: Feb. 24, 2004

(54) DEVICE FOR DETECTING PROPERTIES OF A MOVING WEB OF PAPER WITH AN INFRARED LIGHT SOURCE

(75) Inventor: Ursula Schumacher, Jülich (DE)

(73) Assignee: Metso Paper Automation Oy, Tampere (FI)

(*) Notice: Subject to any disclaimer, the term of this patent is extended or adjusted under 35 U.S.C. 154(b) by 31 days.

(21) Appl. No.: 10/167,114

(22) Filed: Jun. 11, 2002

(65) Prior Publication Data

US 2002/0179840 A1 Dec. 5, 2002

Related U.S. Application Data

(63) Continuation of application No. PCT/DE00/04034, filed on Nov. 16, 2000.

(51) Int. Cl.⁷ .......................... G01N 21/01; G01N 21/35
(52) U.S. Cl. ............................. 250/341.1; 250/359.1; 250/341.8; 356/429
(58) Field of Search .......................... 250/341.1, 341.8, 250/359.1, 548, 559.01, 559.05, 559.06; 356/637, 639, 429, 430, 431

(56) References Cited

U.S. PATENT DOCUMENTS

| | | | |
|---|---|---|---|
| 3,859,538 A | | 1/1975 | Mannonen |
| 4,004,152 A | * | 1/1977 | Obser et al. ............ 250/559.07 |
| 4,186,431 A | | 1/1980 | Engel et al. |
| 4,226,538 A | * | 10/1980 | Van Beeck ................. 356/430 |
| 4,377,746 A | | 3/1983 | Kopineck et al. |
| 4,660,967 A | | 4/1987 | Inokuchi |
| 4,877,326 A | | 10/1989 | Chadwick et al. |
| 4,914,308 A | | 4/1990 | Hochgraf |
| 4,920,265 A | * | 4/1990 | Chase et al. ................. 250/308 |
| 4,943,447 A | * | 7/1990 | Nelson et al. ............... 427/542 |
| 5,064,280 A | * | 11/1991 | Ringens et al. ............ 356/28.5 |
| 5,243,402 A | * | 9/1993 | Weber et al. ................. 356/429 |
| 5,274,243 A | * | 12/1993 | Hochgraf ............... 250/559.41 |
| 5,745,176 A | | 4/1998 | Lebens |
| 5,747,795 A | | 5/1998 | Monney |
| 6,091,501 A | * | 7/2000 | Saikanmaki et al. ......... 356/402 |
| 6,111,651 A | * | 8/2000 | Shakespeare ............... 356/429 |
| 6,452,679 B1 | * | 9/2002 | Workman, Jr. ............. 356/429 |

FOREIGN PATENT DOCUMENTS

| | | | |
|---|---|---|---|
| DE | 19506675 A1 | * 8/1996 | ............ G02B/6/32 |
| GB | 1103491 | 2/1968 | |

* cited by examiner

Primary Examiner—Albert Gagliardi
(74) Attorney, Agent, or Firm—Alston & Bird LLP

(57) ABSTRACT

A device for detecting properties of a moving web of paper, more specifically for production control in the paper making process, comprising an infrared lighting device suited for illuminating the web of paper with infrared light and a detector device for detecting light reflected or transmitted by the web of paper which is provided with a light input portion. The infrared lighting device is provided with a light source in the form of a long, rod-shaped infrared emitter, the light source being accommodated in a housing having a front plate facing the web of paper. An exit window, through which the light from the light source passes to impinge upon the web of paper, is tight-fittingly received in an aperture in the front plate.

8 Claims, 3 Drawing Sheets

Figure 1:
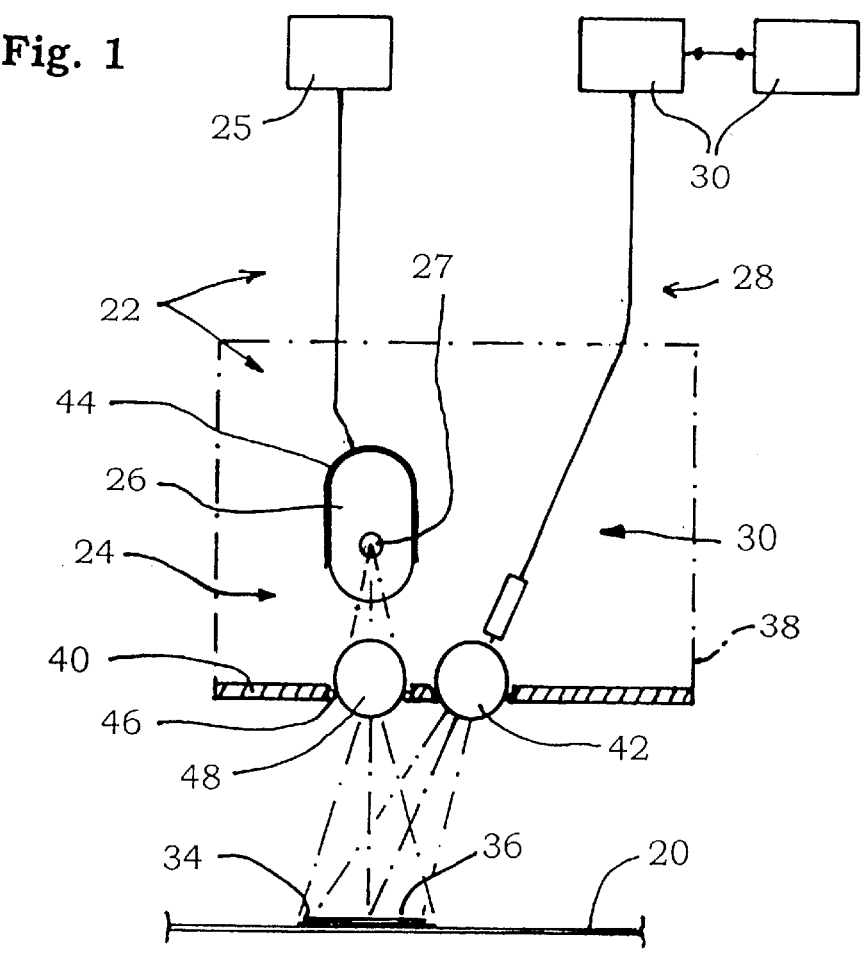

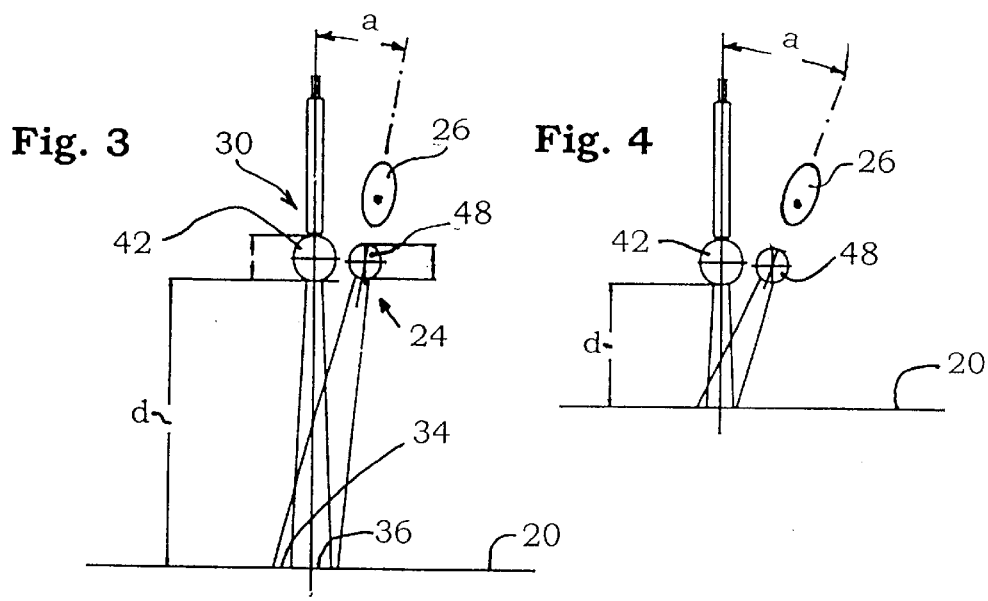
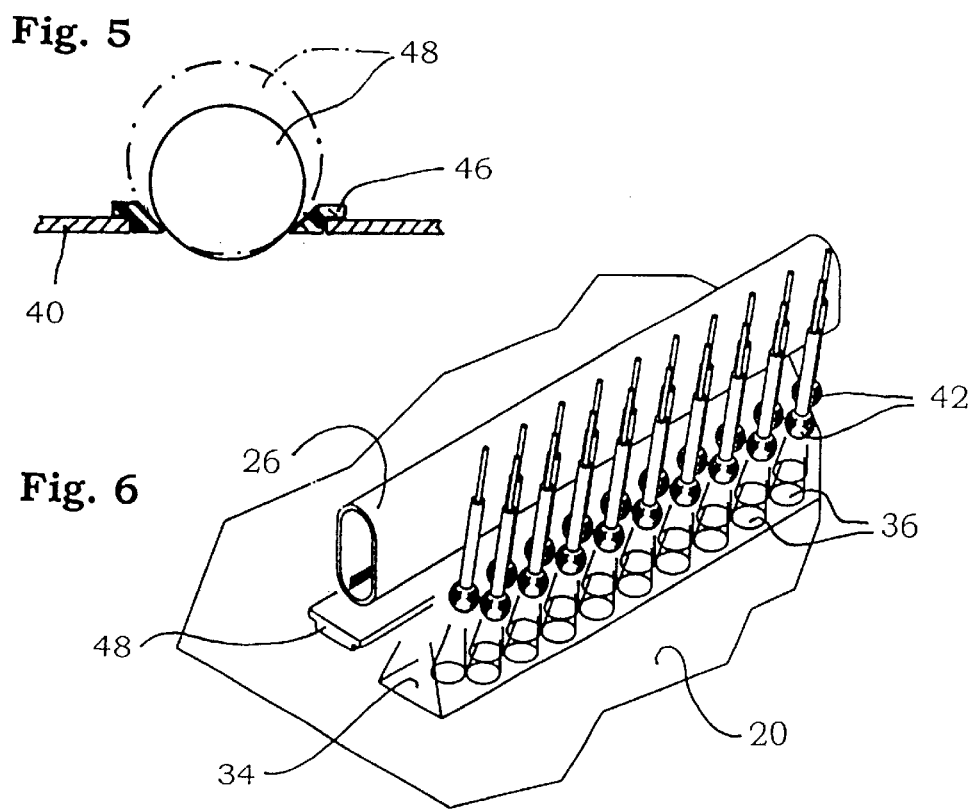

DEVICE FOR DETECTING PROPERTIES OF A MOVING WEB OF PAPER WITH AN INFRARED LIGHT SOURCE

CROSS-REFERENCE TO RELATED APPLICATIONS

This application is a continuation of International Patent Application PCT/DE00/04034 filed Nov. 16, 2000, which is incorporated herein by reference.

FIELD OF THE INVENTION

The invention relates to a device for detecting properties of a moving web of paper, more specifically for production control in the paper making process, having an infrared lighting device operable to illuminate the paper web with infrared light and a detector device for detecting light reflected or transmitted by the paper web, the detector device having a light input portion.

BACKGROUND OF THE INVENTION

A device as described above is disclosed in WO 98/40727, wherein the web of paper is illuminated by an infrared light source that is not described in any detail. A light exit portion for directing light onto the web and a light input portion for receiving light from the web are located on a holding member supported by a crossbar. The light input portion has a plurality of optical waveguides arranged side by side in the form of optical fibers of typically between 50 and 600 micrometers thick. The ends of the fibers are polished and oriented toward the paper web, and the fibers are fastened to the holding member and project therefrom toward the web.

The infrared lighting device is intended to sufficiently illuminate the region of the paper web onto which the light input portion is directed. Reflected or transmitted light can be measured thereby. The web of paper should be illuminated as uniformly as possible, and the light used should be as intensive and homogeneous as possible in the infrared range, more specifically in the so called near-infrared range, i.e., within the range above visible light (>800 nm) and more specifically within the range of 1.5 to 2.5 micrometers. Light in ranges of wavelengths outside of the range detected by the detector device is not required.

The prior art device allows for a high number of measuring dots arranged side by side on the web of paper. Unlike cradles traveling back and forth on crossbars, this device has the advantage that light detection is carried out in a stationary condition relative to the crossbar. Untested regions of the paper web are smaller than with a cradle. In principle, this is an advantage that preferably should be maintained.

BRIEF SUMMARY OF THE INVENTION

The present invention aims at providing an infrared lighting device that is particularly suited for the measurement task in question, that is relatively inexpensive, and that provides precise illumination of the regions in which the measuring dots of the detector device are located in the simplest possible way. Adequate protection from dust and dirt should also be achieved. In the paper making process, considerable amounts of dirt, dust and so on are produced. The infrared lighting device should be configured in such a manner that it hardly becomes dirty and that it can be readily cleaned when dirty. As paper machines often operate without interruption for many months, cleaning should be possible while the paper machine is in operation.

Furthermore, it is the object of the invention to provide a lighting device that requires a relatively small number of parts and that allows easy assembly, reliable operation, and an intense, homogeneous illumination of those regions of the web of paper on which the measuring dots of the detector device are located.

Toward these ends, the present invention provides an infrared lighting device with a light source in the form of a long, rod-shaped infrared emitter contained within a housing, the housing having a front plate facing the web of paper. A tight-fitting exit window is arranged in the front plate through which the light from the light source passes to impinge upon the web of paper.

The long rod-shaped infrared emitter provides the advantage that one single illumination source suffices for a portion of the paper web to be tested that is at least one meter, preferably at least two meters wide. A considerable portion of the web of paper, which typically is many meters wide, can thus be detected by only one source of light. This has a considerable advantage over many individual light sources used for illumination. The number of component parts of the lighting device is considerably reduced, such that assembly, service, and maintenance are simplified. At the same time, the illumination of the web of paper is very good. It is easily possible to adjust the device to accommodate diverse distances between the light exit portion and the web of paper. Finally, the lighting device is easy to clean and hence can be readily maintained in a Typical infrared emitters as they are utilized for the invention are sold as tubular infrared emitters in the trade name of ZKA for example by Heraeus Nobellight GmbH, Kleinostheim, Germany. These emitters are tubes made of quartz glass with at least one internal canal inside of which there is located an electrically heated filament. So-called twin tubular emitters with gold reflector have proved particularly suitable. Emitters of circular tube type with gold reflector are also suitable, though. The manufacturer mentioned also produces these infrared emitters as a halogen emitter and as a short-wave infrared emitter. According to manufacturer information, they are almost exclusively utilized in fields in which heat is needed, e.g., for the drying of paper and cardboard, the drying of printing colors, the drying of lacquers in enameling lines and so on. An application in the field of metrology has not yet become known. A desired one of the aforementioned ranges of wavelengths can be obtained by selecting an appropriate infrared emitter.

The rod-shaped light source is accommodated within a housing that is elongated in the same way as the infrared emitter. The housing is preferably sealed. As a result, dust and dirt are reliably prevented from entering the infrared emitter and its surroundings. Furthermore, the housing assures that the light from the infrared emitter exits only at places at which exit is wanted.

As noted, a tight-fitting exit window through which the light of the light source is incident onto the web of paper is arranged in the front plate of the housing. The window allows for a dust-tight configuration of the housing. The exit window is easy to clean from the outside. It remains clean on the inside, since the housing is closed.

In a preferred embodiment, the exit window is configured as a rod lens. The rod lens has substantially the length of the rod-shaped infrared emitter. By virtue of the rod-shaped infrared emitter in connection with the rod lens, the lighting device is easily made to span a portion of the paper web of at least one meter wide. Furthermore, only very few component parts are needed for the lighting device.

Preferably, the rod lens has the shape of a cylinder. The cylindrical shape has the advantage that it can be readily mounted in the front plate in a tight-fitting manner. Because of the circular cross-section, the rod lens need not be oriented in any particular manner, and the rod lens also resists high changes in temperature. When the materials of which the cylindrical rod lens and the front plate are made are thermally expanding, a relative movement between the lens and the front plate may take place. The portion of the exit window that projects downward can be cleaned with simple means.

In a preferred embodiment, the detector device has a plurality n of spherical lenses. The spherical lenses are tight-fittingly received in apertures in the front plate and are each optically coupled, within the housing, to an allocated optical fiber of the light input portion. The combination of the thus configured light input portion with the infrared lighting device described above proved very suitable for measurement tasks. An adjustment of the measuring dot in the region on the web of paper which is illuminated by the infrared lighting device can be achieved by simple means. The aperture of the optical fibers is corrected or the light is collimated respectively by means of the spherical lenses. The size of the measuring dot on the web of paper can thus be varied; the diameter for example can be varied between 5 mm and 10 mm. In this way, paper can be measured with a sufficient cross sectional resolution of the profile measurement. Depending on the distance from the web of paper, which typically amounts to between 20 and 50 mm, on the size of the measuring dot and on the cross sectional resolution, spheres made of sapphire or of other glasses, which are transmissive to spectroscopy and have a diameter typically ranging from 2 to 10 mm, are used. They are easier to manufacture than the customary lens-shaped convergent lenses and can be more readily fastened and sealed than the latter.

By virtue of the spherical lenses, the optical images on the paper web can be predetermined and controlled with much more precision. As the housing is sealed, the coupling region between the spherical lenses and the optical fibers is protected. The portions of the spherical lenses that are directed toward the web of paper can be easily cleaned. The high hardness of sapphire is advantageous in this regard.

The spherical lenses advantageously are replaceably arranged in the front plate so that spherical lenses of different diameters can be mounted into the front plate. Different images can thus be obtained depending on the purpose of the measurement. The same applies for the rod lens of the infrared lighting device.

By changing the angle formed between the optical axes of the infrared lighting device and of the light input portions, the spacing between the housing and the web of paper can be readily adjusted. The easiest way to achieve this is to adjust the angular position of the infrared emitter relative to the exit window.

It is particularly convenient to have the housing configured in a substantially elongated shape, more specifically to give it a length of at least one meter and preferably a length of at least two meters. The infrared emitter should have an equal length. With the usual widths of paper webs, only a few housings are needed, preferably arranged side by side in a staggered relation on a stationary crossbar, for illumination of the entire web of paper. To permit the exchange of individual housings during the paper making process, at least some of the housings preferably are connected to the crossbar by way of a longitudinal guide in which they are slidable relative to the crossbar. Individual housings can thus be removed from the crossbar without disturbing the paper making process.

Furthermore, it is advantageous to provide a cleaning device designed to clean those portions of the spherical lenses and their surroundings that are accessible from the outside on the front face and that are oriented toward the web of paper. It is thus made certain that dirt, which is inevitable in normal operation of the paper machine, does not restrict the optical conditions.

It is furthermore convenient to provide the outer side of the rod-shaped infrared emitter with a reflector layer, more specifically with a gold reflector layer, and to leave therein an exit region, or an exit slit, which opens toward the exit window. The infrared radiation is thus substantially focused or directed onto the exit window.

BRIEF DESCRIPTION OF THE SEVERAL VIEWS OF THE DRAWING(S)

Figure 2:
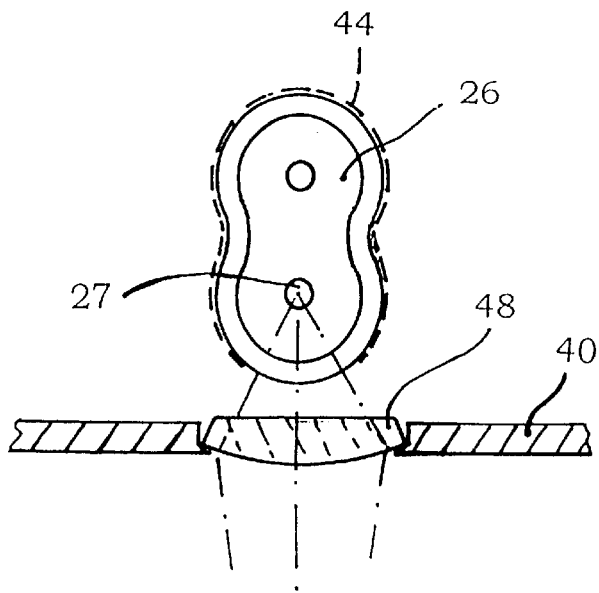
Figure 7:
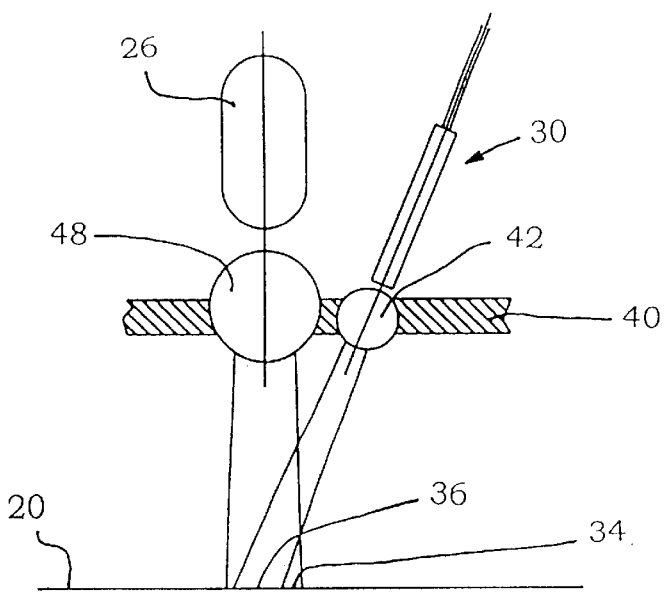
Figure 8:
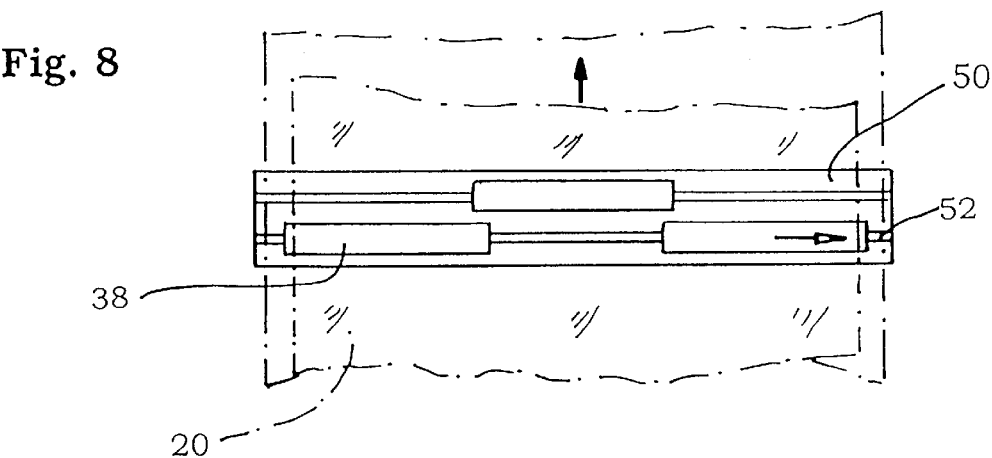
Figure 9:
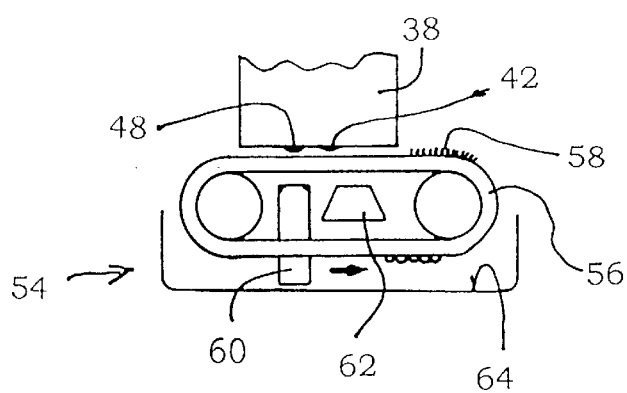

Having thus described the invention in general terms, reference will now be made to the accompanying drawings, which are not necessarily drawn to scale, and wherein:

FIG. 1: is a schematic side view of a device for detecting properties of a moving web of paper with an infrared lighting device in accordance with the invention, FIG. 2: is an illustration according to FIG. 1 of another configuration of the infrared emitter, the other parts of FIG. 1 not being repeated, FIG. 3: is a side view explaining the beam path, FIG. 4: is a view according to FIG. 3, but in another angular position, the setting of the illuminating dot being recognizable in connection with FIG. 3, FIG. 5: is a sectional view of a front plate similar to FIG. 1 illustrating the arrangement and seal of the exit window configured as a cylindrical rod lens, FIG. 6: is a perspective view of a web of paper onto which an infrared lighting device is directed and provided with light input portions according to the configuration according to FIG. 1, FIG. 7: is a view similar to FIG. 3, but this time in another arrangement, FIG. 8: is a bottom view of a conveyed web of paper shown in dash-dot line on a crossbar and provided with three housings and FIG. 9: is a schematic side view of a cleaning device located underneath a housing.

DETAILED DESCRIPTION OF PREFERRED EMBODIMENTS

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

FIG. 1 shows a device for detecting physical and/or chemical properties of a moving web of paper 20, the motion being indicated by an arrow. It has an infrared lighting device 22 which is provided, in the exemplary embodiment of concern, with a light exit portion 24, with a source of infrared light 26 in the form of a rod emitter, and with an electric control unit 25. The rod emitter comprises a quartz tube which is closed at its end and whose height amounts to approximately 27 mm, its width to about 21 mm. A filament 27 is located within the quartz tube.

The device also has a detector device 28 provided with a light input portion 30 and with an evaluation unit 32 arranged downstream thereof and including for example a polychromator with an infrared photoconductor array in the form of a matrix connected downstream thereof and an electronic equipment.

By means of the infrared lighting device 22, the web of paper 20 is illuminated in the form of a very long, thin line that may also be termed a slit. Accordingly, one single very long illuminating dot 34, as much as 1 meter long or even two meters long or more, is generated. A plurality of light input portions 30, which acquire the information of one measuring dot or receiving dot 36 located within the illuminating dot 34, are allocated to this unique illuminating dot. The dot 34 is substantially shaped like a very long rectangle whereas the dots 36 are circular in shape, as can be seen in FIG. 6.

The overall infrared lighting device 22 and the individual light input portions 30 are accommodated in a housing 38 which is sealed from the outside. It has one front plate 40 that faces the web of paper 20 and need not necessarily be a plate but can be any other shape. It is arranged in immediate proximity to the web of paper.

As shown in the Figures, more specifically in FIG. 6, a plurality of spherical lenses 42 is tight-fittingly received in apertures formed in the front plate 40. The number of spherical lenses 42 amounts to n. FIG. 6 shows a total of n=19 such spherical lenses 42 which are each assigned optical fibers of the detector device 28. The arrangement is regular. Within the illuminating dot 34, individual, smaller measuring dots 36 are obtained on the web of paper 20.

The quartz tube of the infrared emitter has a reflector 44 which is arranged on the outside in the exemplary embodiment shown and which consists of a layer of gold. The reflector encases the quartz tube completely except for a small slit through which light exits. In FIG. 1, the reflector 44 is illustrated in accordance with its actual configuration, i.e., in full line. In FIG. 2 it is shown in dashed line for purposes of clarity, but it will be understood that the reflector in actuality constitutes a continuous uninterrupted layer.

In housing 38, an exit window 48 is arranged in close proximity to the individual spherical lenses 42; in FIG. 1 the window is configured as a cylindrical rod lens, in FIG. 2 as a rod-shaped convergent lens. FIG. 5 shows how the exit window, which is here configured as a cylindrical rod lens as sold for example by Edmund Scientific under the name Micro-Rod, is tight-fittingly inserted from the top into an elongate aperture in the front plate. For this purpose, seals 46 forming an inclined supporting surface are arranged in the aperture of the front plate. As a result thereof and as shown in FIG. 5, rod lenses of various diameters can be tight-fittingly inserted. The rod lens can move relative to the front plate 40 when thermal expansion occurs.

It can be seen from FIGS. 3 and 4 that the measuring device may be adjusted for various spacing distances between the web of paper 20 and the housing by changing the angular position of the infrared emitter 26 relative to the exit window. FIG. 4 shows that the spacing between the spherical lenses 42 and the exit window 48 and the web of paper can be changed by increasing the angle a. FIG. 3 shows a condition with a large spacing d, FIG. 4 a condition with a small spacing d.

The exit window 48 is accessible from the bottom. The window partially protrudes downward from the lower side of the housing 38. The spherical lenses 42 also project downward.

FIG. 7 shows an arrangement similar to that in FIGS. 3 and 4 except that the infrared emitter 26 and the individual light input portions 30 have been switched in position. Again, the exit window 48 has optical properties, being configured as a convergent lens, in this case as a cylindrical rod lens. The lens almost collimates the light so that an elongated illuminating dot 34, about 5 to 10 mm wide, is obtained. Thanks to its highly symmetrical configuration which in cross-section resembles more a sphere, the rod lens is less prone to breaking under thermal tensions than a plate as shown in FIG. 6.

FIG. 8 shows a bottom view through a web of paper 20, shown in dash-dot line, of a stationary crossbar 50 that is connected to a part of a paper machine which is also shown in a dash-dot line. Rails 52 are arranged on the bottom side of the crossbar 50. Elongated housings 38 are hanging from the rails, light exit portions 24 and light input portions 30 being arranged in the housings in accordance with FIGS. 2, 6 or 7. The configuration according to FIG. 8 is preferably intended to be used with the rod-shaped infrared light sources 26 according to FIGS. 6 and 7. To span a web of paper 20 of many meters wide, several housings 38 are arranged in a staggered pattern so that the entire width of the paper web 20 can be measured on a continuous basis.

FIG. 9 shows a cleaning device that is only shown in principle. It shows a housing 38 from the bottom of which spherical lenses 42, 44 or a rod lens 48 protrude slightly. The cleaning device 54 has an endless belt 56 that is supported on the right and on the left side thereof by two rolls and which is driven, the drive occurring in the direction of the arrow. Brushes 58 for cleaning the bottom face of the front plate 40, and more specifically those parts of the spherical lenses 42, 44 that are accessible from underneath, are for example located on the belt. Drying devices and so on are also provided on the belt 56. For cleaning, a cleansing fluid is sprayed from the bottom onto the front face 40 by means of a spraying device 60, the fluid being sucked off again by a suction device 62. A trough 64 is located underneath the cleaning device 54, so that other parts are not soiled in the process.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for detecting properties of a moving web of paper, comprising:

a housing having a front plate facing the web of paper;

an infrared lighting device operable to illuminate the web of paper with infrared light and a detector device for detecting light reflected or transmitted by the web of paper, the infrared lighting device comprising a rod-shaped infrared emitter having a longitudinal axis oriented parallel to the paper web, the infrared emitter being accommodated within the housing; and an exit window arranged in the front plate of the housing such that light emitted by the infrared emitter passes through the window and is incident on the paper web, the exit window comprising a circular cylindrical rod lens whose length substantially equals that of the infrared emitter and which is replaceably inserted in an aperture formed in the front plate such that circular cylindrical rod lenses of different diameters can be inserted, the cylindrical rod lens being received in the aperture in a tight-fitting manner so that the housing is sealed from debris.

2. The device of claim 1, wherein the housing is elongated having a length of at least one meter.

3. The device of claim 2, further comprising a plurality of said housings and a crossbar oriented across the moving web of paper, the housings being arranged side-by-side on the crossbar, each housing being retained in a longitudinal guiding device and being slidable relative to the crossbar along the longitudinal guiding device.

4. The device of claim 1, further comprising a cleaning device operable to clean those portions of the exit window and surrounding surfaces that are accessible from outside the housing on the front plate.

5. The device of claim 1, wherein the infrared emitter has a reflector layer that substantially prevents emission of light from the emitter in any direction except toward the exit window in the housing.

6. The device of claim 1, wherein the infrared emitter is at least one meter in length.

7. The device of claim 1, wherein the infrared emitter is at least two meters in length.

8. A device for detecting properties of a moving web of paper, comprising:

a housing having a front plate facing the web of paper;

an infrared lighting device operable to illuminate the web of a paper with infrared light and a detector device for detecting light reflected or transmitted by the web of paper, the infrared parallel to the paper web, the infrared emitter being accommodated within the housing; and an exit window arranged in the front plate of the housing such that light emitted by the infrared emitter passes through the window and is incident on the paper web, the exit window comprising a cylindrical rod lens whose length substantially equals that of the infrared emitter and which is replaceably inserted in an aperture formed in the front plate such that cylindrical rod lenses of different diameters can be inserted, the cylindrical rod lens being received in the aperture in a tight-fitting manner so that the housing is sealed from debris; and wherein the detector device includes a light input portion provided with optical fibers arranged in the housing and wherein a plurality n of spherical lenses are received in apertures in the front plate in a tight-fitting manner, each spherical lens being optically coupled within the housing to an allocated optical fiber of the light input portion.

* * * * *

UNITED STATES PATENT AND TRADEMARK OFFICE
CERTIFICATE OF CORRECTION

PATENT NO. : 6,696,685 B2 Page 1 of 1
DATED : February 24, 2004
INVENTOR(S) : Schumacher It is certified that error appears in the above-identified patent and that said Letters Patent is hereby corrected as shown below:

Title page,
Insert Item [30], as follows:
-- [30] Foreign Application Priority Data
December 11, 1999 (DE) 199 59 763.4 --.

Column 2,
Line 26, after "in a" insert -- clean condition. --.

Signed and Sealed this

Eighteenth Day of May, 2004

JON W. DUDAS
*Acting Director of the United States Patent and Trademark Office*